United States Patent
Pinkerton et al.

(10) Patent No.: US 11,806,479 B2
(45) Date of Patent: Nov. 7, 2023

(54) METHOD AND SYSTEM FOR INFLUENCING EMOTIONAL REGULATION THROUGH ASSESSMENT, EDUCATION, AND MUSIC PLAYLIST APPLICATIONS

(71) Applicant: Music 4 Life Technology, Inc., Las Vegas, NV (US)

(72) Inventors: Judith Ann Pinkerton, Las Vegas, NV (US); Richard Alan Duggan, Henderson, NV (US)

(73) Assignee: MUSIC 4 LIFE TECHNOLOGY, INC., Las Vegas, NV (US)

( * ) Notice: Subject to any disclaimer, the term of this patent is extended or adjusted under 35 U.S.C. 154(b) by 875 days.

(21) Appl. No.: 16/666,378

(22) Filed: Oct. 28, 2019

(65) Prior Publication Data
US 2020/0129728 A1    Apr. 30, 2020

Related U.S. Application Data

(60) Provisional application No. 62/751,183, filed on Oct. 26, 2018.

(51) Int. Cl.
A61M 21/02    (2006.01)
A61M 21/00    (2006.01)
(Continued)

(52) U.S. Cl.
CPC ............ *A61M 21/02* (2013.01); *A61B 5/165* (2013.01); *G06F 3/165* (2013.01); *G09B 19/00* (2013.01);
(Continued)

(58) Field of Classification Search
None
See application file for complete search history.

(56) References Cited

U.S. PATENT DOCUMENTS 10,346,754 B2    7/2019 Ritchie et al.
2010/0312042 A1    12/2010 Anderson et al.
(Continued)

FOREIGN PATENT DOCUMENTS

EP    2661301 B1    8/2015

OTHER PUBLICATIONS

"Judith Pinkerton, LMPT, MT-BC", https://judithpinkerton.com/.

*Primary Examiner* — Christine H Matthews
(74) *Attorney, Agent, or Firm* — SNELL & WILMER L.L.P.

(57) ABSTRACT

A method of music therapy informed processes provides an effective online process to help a user regulate their mood through appropriate music selection choices. The method offers mood and music assessments to evaluate the user's mood, music preferences, goals, and understanding of the correlation between various moods and music. A mood sequence formula (MSF) is subsequently created to generate stylized and personalized music medicine pill (MMP) playlists. With additional recommendations of music exercise routine/regimen (MER) to the user, the method delivers therapeutic MMP playlists of the music therapy informed process with personalized music to manage physiological and behavioral responses, emotional regulation, performance and emotional intelligence. Using daily tracking and specific measurement data of biometrical and physiological devices, the user can track the progress and thus enable the method to fine tune the MSF and MMP playlists for the best effectiveness of the music therapy informed method.

19 Claims, 21 Drawing Sheets

(51) Int. Cl.
*G06F 3/16* (2006.01)
*G09B 19/00* (2006.01)
*A61B 5/16* (2006.01)

(52) U.S. Cl.
CPC .............. *A61M 2021/0016* (2013.01); *A61M 2021/0027* (2013.01); *A61M 2205/3553* (2013.01); *A61M 2205/50* (2013.01)

(56) References Cited

U.S. PATENT DOCUMENTS

2012/0233164 A1    9/2012   Rowe et al.
2016/0055420 A1*   2/2016   Karanam ............. A61B 5/7246
                                                    700/52

* cited by examiner

METHOD AND SYSTEM FOR INFLUENCING EMOTIONAL REGULATION THROUGH ASSESSMENT, EDUCATION, AND MUSIC PLAYLIST APPLICATIONS

The current application claims a priority to the U.S. Provisional Patent application Ser. No. 62/751,183 filed on Oct. 26, 2018. The current application is filed on Oct. 28, 2019 while Oct. 26, 2018 was on a weekend.

FIELD OF THE INVENTION

The present invention relates to music therapy informed methods. More specifically, the present invention is a method and system to improve a user's emotional regulation, physiological and behavioral responses through assessment, education, and therapy applications using music playlists that are created according to human mood sequence formulas.

BACKGROUND OF THE INVENTION

Music therapy is a clinical and evidence-based use of music interventions in which music is applied within a therapeutic relationship to address physical, emotional, cognitive, and social needs of individuals, according to American Music Therapy Association. Conventionally, a qualified music therapist or certified music professional assesses the strengths and needs of a user, and then provides a specific treatment, which includes creating, singing, moving to, and/or listening to music. In recent years, significant progress has been made in both the research and clinical application of music as a form of treatment. It has valuable therapeutic properties, thus, suitable for the treatment of several diseases. The term "music medicine" is used for therapeutic purpose of music applied as medicine, which is the focus on a scientifically, artistically and clinically based approach to music. Through musical involvement in the therapeutic context, the user's abilities are strengthened and transferred to other areas of their lives. Music therapy also provides avenues for communication that can be helpful to those who find it difficult to express themselves in words. Because the right type of music activates the reward center and triggers the release of dopamine, music therapy can reduce stress, increase oxytocin levels, and provide natural pain relief. Over the years, music therapy has proven its effectiveness in many areas including child development, emotional growth, improving symptoms of depression, the quality of life, academic performance, promoting behavior change, engaging human minds, improving autism and social skills, and expressing feelings.

In conventional systems, individuals would often treat illnesses with opioids and/or intrusive medical healing methods that may result in undesirable post-procedure side effects such as addiction. Individuals would opt for music therapy sessions as an alternative to opioids, but a music therapy session normally requires the individual to schedule an appointment with a certified music therapist. Commuting to the therapist's office during business hours can add to the inconvenience. For a specific in-office therapist in an area, who seems like a perfect fit, however, the user may have to wait for a long time before starting therapy due to accommodation issues. Further, if the user does not like talking as a way of expressing feelings and addressing mental health issues, in-person psychotherapy may be not a good fit for the user. And added to all these shortcomings, the conventional music therapy can be very expensive, and the associated high cost may not be covered by medical insurance policies.

Thus, it is an objective of the present invention to improve the conventional music therapy informed methods and systems by providing a streamlined music therapy informed process. The method and process are referred to as "music therapy informed" and not "music therapy" because a certified music therapist is not automatically present during the method and process on the user's PC device. When a music therapist is present, this method and process is a music therapy method. Because PC devices do not offer a certified music therapist throughout the present invention, this method is referred to as "music therapy informed." The present invention helps the user regulate their mood through appropriate music selection choices. The present invention offers various quizzes, training tools, tests, and exercises to the user to advance personal training. While listening, the user is occasionally queried as to their mood and the type of music selection to which the user is listening. As long as the user is correctly assessing their mood and music selection choice, the present invention blends into the background and the user receives the benefit of their music choices. Should the user not correctly assess their mood or is categorizing music incorrectly according to the mood labeling system, the present invention provides additional support to assist the user, including self-directed training courses and, if needed, remote consulting sessions with certified music therapists or music therapy informed therapists/professionals. The present invention takes form of a mobile application that includes interfaces with app-based emotional intelligence, physiological, behavioral and performance tests to gauge/rank the biological, psychological and behavioral impact of different music, empowering the user to maximize their benefits. Additionally, the present invention will offer suggestions of essential oils that may enhance various mood states.

SUMMARY OF THE INVENTION

A music therapy informed method provides an effective and streamlined process to help a user regulate their mood through appropriate music selection choices. The music therapy informed method is an online platform that delivers therapeutic playlists of informed and personalized music to manage the user's physiological and behavioral responses, emotional regulation, performance and positive emotional intelligence, etc. Additionally, the music therapy informed method offers an efficient and effective process for identifying and categorizing music selections being listened to by a user using a plurality of mood labels and identifying opportunities to improve the user's mood by assigning one or more music selections into a given specialized playlist.

The music therapy informed method offers mood and music assessments to evaluate the user's mood, music preferences, goals, and understanding of the correlation between various moods, behaviors, performance, biology, and music. Various questionnaires, quizzes, training tools, tests, and exercises are incorporated in the music therapy informed method to help the user advance personal training and gain the best use of the method. While listening, the user is occasionally queried as to their mood and biological response with the type of music selection to which the user is listening. As long as the user is correctly assessing their mood and music selection choice, the music therapy informed method blends into the background and the user receives the benefit of their music choices. Should the user not correctly assess their mood or is categorizing music incorrectly according to the mood labeling system, the present invention provides additional support to assist the user, which includes self-directed training courses, and/or, if needed, remote consulting sessions with certified music therapists or music therapy informed therapists/professionals.

Upon receiving all input and personal data, the music therapy informed method creates a mood sequence formula (MSF) which is subsequently used to generate stylized and personalized music medicine pill (MMP) playlists. The MSF is based upon research studies and clinical evidence that support the creation of effective MMP playlists accessing all music genres. Minimally, a specific playlist is populated with the target music associated with at least one user's mood that needs to be improved. Then the MMP is identified to sequence the mood music pulled from these playlists to generate the MMP playlist. Further, the music therapy informed method enables a user to create and deliver personalized music content based on preferred music selections, and/or desired input goals, following the MSF.

With additional recommendations of music exercise routine/regimen (MER) to the user, the method delivers therapeutic MMP playlists of informed and personalized music to manage physiological and behavioral responses, emotional regulation, performance and positive emotional intelligence. Using daily tracking and specific measurement data of biometrical and physiological devices, the user can track the progress and thus enable the method to fine tune the MSF and MMP playlists for the best effectiveness of the music therapy informed method.

The music therapy informed method takes the form of a mobile application that includes interfaces with app-based emotional intelligence, physiological, behavioral and performance tests to gauge/rank the biological, psychological and behavioral impact of different music, empowering the user to maximize their benefits. Further, the music therapy informed method provides recommendations and guidance for aromatherapy applications that enhance the music therapy informed process.

DETAIL DESCRIPTIONS OF THE INVENTION

Figure 1:
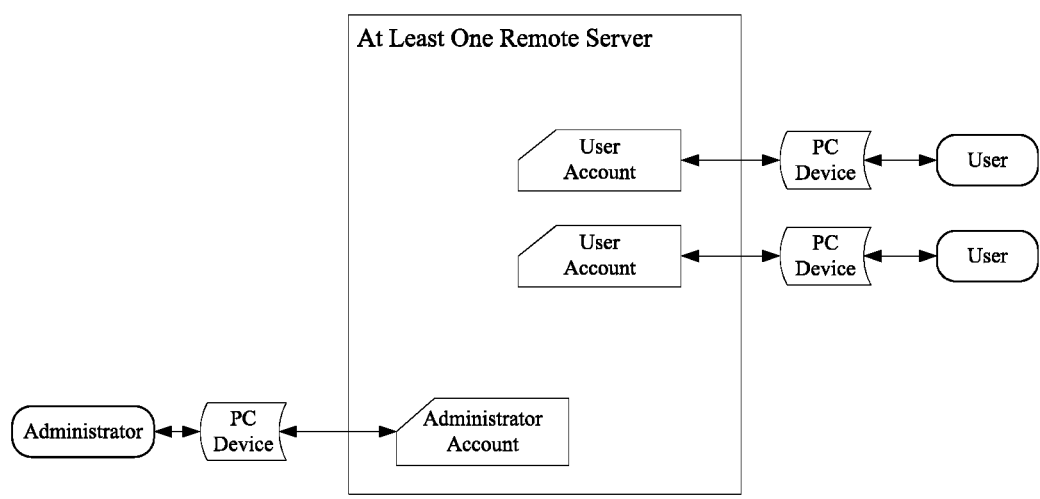
FIG. 1 is a system diagram of the present invention.

All illustrations of the drawings are for the purpose of describing selected versions of the present invention and are not intended to limit the scope of the present invention.

As can be seen in FIGS. 1-21, the present invention is a method and system for providing music therapy informed process and managing emotional regulation. More specifically, the music therapy informed method of the present invention is an online platform that delivers therapeutic playlists of informed and personalized music to manage physiological and behavioral responses, emotional regulation, performance and positive emotional intelligence. In the preferred embodiment of the present invention, the music therapy informed method offers an efficient and effective process for identifying and categorizing music selections being listened to by a user using a plurality of mood labels and identifying opportunities to improve the user's mood by assigning one or more music selections in a given specialized playlist. Additionally, the music therapy informed method enables a user to create and deliver personalized music content based on preferred music selections, and/or desired input goals. Further, the music therapy informed method provides recommendations and guidance for aromatherapy applications that enhance the music therapy informed process.

In the system of the music therapy informed method of the present invention, the plurality of mood labels includes, but is not limited to, U (Unsettled), S (Soothed), or E (Energized), Th (Theme), Tr (Transition), etc. The U—Unsettled music is referred to the category of music that jangles nerve ends, bestirs the soul, and blackens a mood. For Unsettled music category, the moods associated with include, but are not limited to, anger, anxiety, depression, sadness, uneasiness, uncomfortableness, etc. The S—Soothed music is defined as the category of music that numbs, calms, and/or deeply relaxes, with associated moods including, but not limited to, peacefulness, relaxation, calm, ease, comfort, tranquility, etc. The E—Energized music refers to the category of music that puts physiological and psychological "fizz" in the user's life, and includes, but is not limited to, happiness, joy, enthusiasm, optimism, positiveness, activeness, invigoration, energy, etc. The Th—Theme music is the user's personal music with specific emotional attachment and life story experience, while the Tr—Transition music include multiple elements of aforementioned USE music in a single piece of music.

The music therapy informed method creates or assists the user to create playlists, called Music Medicine Pills (MMP), each of which comprises a plurality of music pieces that are selected from mood music categories including, but not limited U, S, E, Th, Tr. Each MMP is used by the user to manage the user's daily emotional regulations, improve the user's mood, biology, emotional intelligence, performance, behavior, and/or enhance healing with the user's psychological illness. The goal of the music therapy informed method is to base user's music listening habits around playlists that correspond with each category, thus producing a balanced music diet, as well as an awareness of how music affects a person emotionally. The MMP playlists are created in accordance with a Mood Sequence Formula (MSF) that is generated based on at least one user assessment, which evaluates and identifies the user's listening habits, personal mood music experiences, understanding of the association of music with mood, personal goals, etc. Based upon music genre preferences indicated by the user in the assessment, the method provides specific music selections to the user to listen to and indicate which mood each piece of music makes the user feel. Depending upon the user's answer, the music selection will be assigned to a specialized playlist with at least one music label such as Th, Tr, U, S, E, or declared an "off-target", incorrect, response. Five examples of this process are listed below:

Example 1

"Struggle Within" by Metallica belongs in the U playlist. If the user does not assign the music piece as U but instead declares it as S or E or Th, this would be an off-target response. Then more music selections will be provided to test the user to determine if the user is capable of assigning music according to correct mood music label category. If the user continues to be off-target, the user will be referred to tutorial videos or eCourses to learn more about the mood music categories, and/or recommend the user to contact a music therapy informed professional for further assistance.

Example 2

"Forever" by Hilary Stagg belongs in the S playlist. If the user does not assign it as S but declares it as U, E, or Tr, this would be an off-target response. Then the user will be tested with more music selections. If the user continues to be off-target, the user will be referred to tutorial videos or eCourses to learn more about the mood music categories, and/or recommend the user to contact a music therapy informed professional for further assistance.

Example 3

"Happy" by Pharrell Williams belongs in the E playlist. If the user does not assign it as E, but declares it as U, or S, this would be an off-target response, then more music selections will be used to test the user If the user continues to be off-target, the user will be referred to tutorial videos or eCourses to learn more about the mood music categories, and/or recommend the user to contact a music therapy informed professional for further assistance.

Example 4

"Starting Over" by Macklemore belongs in the U, or Th playlist. If the user does not assign it as U, or Th, but declares it as S, or E, this would be an off-target response, then more music selections will be used to test the user. If the user continues to be off-target, the user will be referred to tutorial videos or eCourses to learn more about the mood music categories, and/or recommend the user to contact a music therapy informed professional for further assistance.

Example 5

"Flash Dance" by Irene Cara belongs in the E, or Tr playlist. If the user does not assign it as E, or Tr, but declares it as U, or S, this would be an off-target response, then more music selections will be used to test the user. If the user continues to be off-target, the user will be referred to tutorial videos or eCourses to learn more about the mood music categories, and/or recommend the user to contact a music therapy informed professional for further assistance.

The MSF (Mood Sequence Formulas) used in the present invention is based upon research studies and clinical evidence that support the creation of effective MMP playlists accessing all music genres. Minimally, the U-S-E playlists are populated with the target music, then a specific MFS is identified to sequence the mood music pulled from these playlists to generate a new playlist, which becomes an MMP. The MMP playlists are created uniquely from foundational research studies called the Capurso Study and Sentic Cycles as well as Music 4 Life clinical evidence surveying MMP responses from six hundred three patients in residential addiction treatment centers in the United States.

The results of the Capurso Study established an index of musical selections of known psychological value, which many college and high school instructors named compositions, including, but not limited to, instrumental music, solo or ensemble, and vocal other than English, for no more than 3-4 minutes, associated with six mood categories, which are 1.) agitated, 2.) depressed; 3.) eerie, 4.) relaxing, 5.) reverent, and 6.) happy. 105 classical compositions were tested with 1075 non-musical students. Each selection received testing from 100 to 700 listeners. Two minutes elapsed between selections, talking on any subject not related to music listening. Then each listener was asked if he/she was ready for the next piece without bias from the previous piece. The Capurso Study began a volume of research reporting that music selections create desired emotional effects on listeners.

A Sentic Cycle is a biological mood sequence utilizing the neuroscience mechanism and theory developed by Dr. Manfred Clynes, which did not use music. This therapeutic and preventive method of generating and experiencing a sequence of emotions begins first with anger, then hate, grief, love, sex, joy, and finally reverence. Enrolled individuals listened to a click track guiding their "pure quality" expression of each emotion on a daily basis. The Sentic Cycle is described as a long touch composition, performed by finger and arm pressure in a sitting position, with the rest of the body quiet, to effectively generate these emotions in a sequence. When the individual was able to reach a consistent neuro-muscular response, the individual experienced a pure state of emotion without repressing it.

Sentic Cycle treatments are utilized for the emotional care for oncology patients, alcoholism, chemical dependency, and suicide prevention. Challenges that a patient would experience were found to be mitigated by applying Sentic Cycles to psychosomatic problems, character structure, phobias, general anxiety, and depression. The following Sentic Cycle outcomes are very similar to outcomes applying the Music 4 Life® MMP method. The effects of each Sentic Cycle engaged the functions of 1.) practically effortlessly changing emotions, 2.) cathartic release of repressed emotions, 3.) reveal what emotion(s) may be problematic, 4.) enjoying all the emotions, favoring some, and 5.) body awareness for each emotion. After performing a Sentic Cycle, which lasted approximately 26 minutes, the individual experienced well-being, peace, energy and centeredness for 10-24 hours; dissipated anxiety and nervousness; improved sleep; and increased creative and spontaneous functioning.

When an individual continued using Sentic Cycles, three to four times per week, in about two to three weeks the tendency was to 1.) balance the intensity of emotions that arouse those that were repressed and problematic, and decrease the intensity of those too strong; 2.) develop emotional fluidity, as opposed to being in an emotional rut, being stuck in one emotion; 3.) increase self-esteem, self-reliance, energy, heighten communication with others, and exert greater control; 4.) improve the ability to give and receive through being in touch with the range of emotions, a sense of belonging and sharing; 5.) penetrate the character structure for greater understanding; and 6.) improve the experience of the arts and music. Individuals suffering from emotional problems continued using Sentic Cycles according to the severity of the condition, as many as several cycles/day. Tendencies after one to eight weeks were to: 1.) assist the remission of psychosomatic symptoms of emotional origin; 2.) potentially deal with particular emotional problems such as phobias; 3.) decrease insomnia without medication; and 4.) potentially deal with moderate and light depression. Long-term effects of Sentic Cycles, after at least six months of regular use, included positive changes of the ability to communicate, the quality of relationships, the sense of well-being, and the joie de vivre—"joy of living."

Patients in a total number of 603 in residential addiction treatment centers reported positive effects of using one 30-minute MMP playlist linking 11 songs with a script, representing mixed genres of alternative, metal, Christian, world, indie, rock, soul, pop, new age, classical and soundtrack. The reported results include 94% self-reported improved emotional intelligence with 91% self-reporting a shift into feeling more soothed and energized moods. The following are five examples illustrating the music therapy informed method that uses MSF to generate MMP playlists for specific users:

Example A

Through assessments, a problem activity of daily living for a user was identified as sleep problem and the target goal for the user was to be able to sleep through the night. Using the present invention, the MSF for the use was identified as U→S→E→S. The recommended Mood Exercise Routine/Regimen (MER) was to listen daily for two weeks in the evening at least 30 minutes before falling asleep. The MMP of U.S.E.S. playlists were generated by the music therapy informed method with these moods and mood music played nonstop in the following sequence: 1.) U—anxiety—"Wings of Karma" by Mahavishnu Orchestra, 2.) S—peaceful—"Adagio for Strings" by Albinoni, 3.) E—happy—"In the Mood" by Glenn Miller, 4.) S—relaxed—"Canon in D" by Pachelbel.

Example B

Through assessments, a problem activity of daily living for another user was identified as having no motivation and the target goal for the user was to be motivated to do housework or other physical workouts. Using the present invention, the MSF for the use was identified as U→S→E. The recommended MER was to listen daily for two weeks at the time of day when feeling most unmotivated. The MMP of U.S.E. playlists were generated by the music therapy informed method with these moods and mood music played nonstop in the following sequence: 1.) U—depressed, bored/tired—"Shifter" from Black Aria by Glenn Danzig, 2.) S—calm—"Media Vita in Morte Sumus" by Benedictine Monk, 3.) E—enthusiastic—"Practice Makes Perfect" by Michael Franks.

Example C

Through assessments, a problem activity of daily living for another user was identified as road rage and the target goal for the user was calm driving. Using the present invention, the MSF for the use was identified as U→S→E. The recommended MER was to listen daily for two weeks in the evening and/or morning. Also, have available while driving the S playlist of music that has conditioned user into immediate calm, to be used as needed. The MMP of U.S.E. playlists were generated by the music therapy informed method with these moods and mood music played nonstop in the following sequence: 1.) U—angry—"Unleashed" by Pinkerton/Neiman, 2.) S—content—"The Cello's Song" by David Arkenstone, 3.) E—optimistic—"Joy" from MEE™ Concert by Pinkerton/MacIntosh.

Example D

Through assessments, a problem activity of daily living for another user was identified as meditating difficulty and the target goal for the user was meditating easily. Using the present invention, the MSF for the use was identified as U→S. The recommended MER was to listen daily for two weeks just before meditating. Also, have available while driving the S playlist of music that has conditioned user into immediate calm, to be used as needed. The MMP of U.S. playlists were generated by the music therapy informed method with these moods and mood music played nonstop in the following sequence: 1.) U—anxiety—"Angst" from MEE™ Concert by Pinkerton/MacIntosh, 2.) S—tranquil—Jeffrey Thompson, "Yik" from Egg of Time.

Example E

Through assessments, a problem activity of daily living for another user was identified as relaxing difficulty and the target goal for the user was relaxing easily. Using the present invention, the MSF for the use was identified as E→S. The recommended MER was to listen daily for two weeks just before needing to relax. Also, have available while driving the S playlist of music that has conditioned user into immediate calm, to be used as needed. The MMP of U.S.

playlists were generated by the music therapy informed method with these moods and mood music played nonstop in the following sequence: 1.) E—enthusiastic—"Hallelujah" by Clark Sisters, 2.) S—relaxed—"The Oh of Pleasure" by Ray Lynch.

Figure 2:
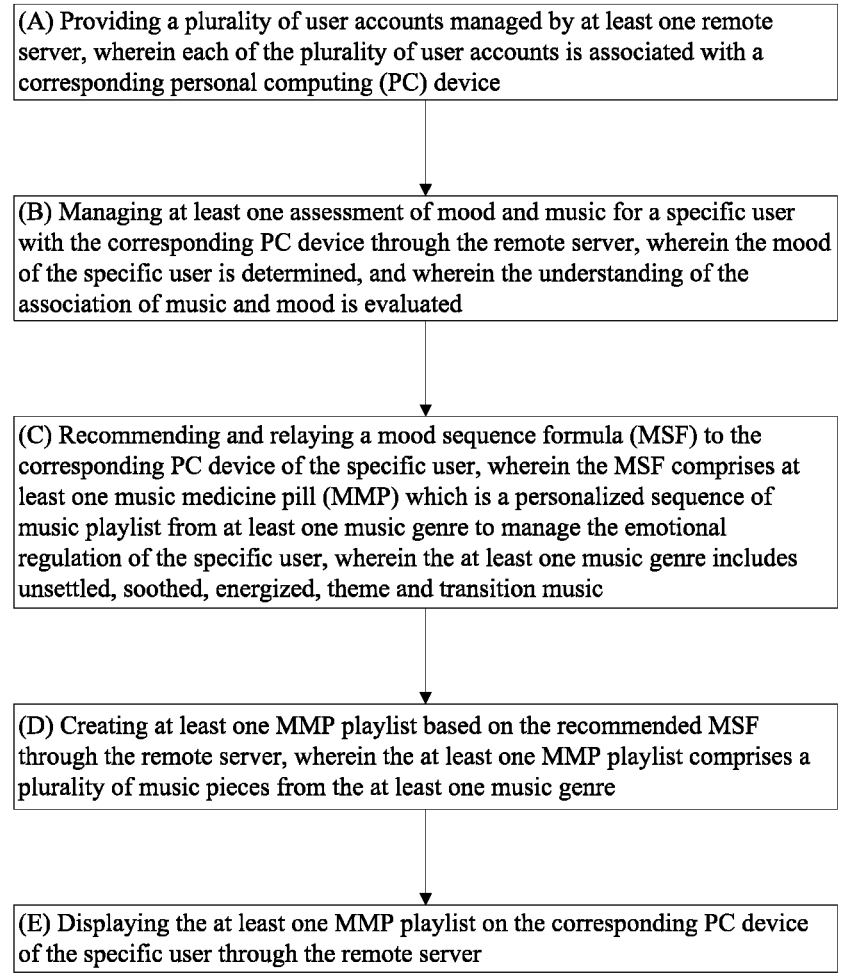
FIG. 2 is a flowchart diagram of the overall process used in method of the present invention.

As can be seen in FIG. 1, the method of the present invention provides an online music therapy informed platform between multiple users. To accomplish this, the method of the present invention associates each of the plurality of users with a unique user account from a plurality of user accounts that is managed by at least one remote server (Step A) as seen in FIG. 2. Each of the plurality of user accounts is associated with a corresponding user personal computing (PC) device. The corresponding user PC device allows a user to interact with the present invention and can be, but is not limited to, a smartphone, a smart watch, a laptop, a desktop, a server computer, or a tablet PC. The users of the user accounts may include relevant parties such as, but are not limited to, individuals, consumers, corporations, patients, entities, hospitals, health providers, music therapy informed professionals, certified music therapists, licensed music therapists, doctors, nurses, insurance companies, care center professionals, administrators, etc. Further, the at least one remote server is used to manage HIPAA (Health Insurance Portability and Accountability Act of 1996) compliant online music therapy informed method between the plurality of user accounts. The remote server can be managed through an administrator account by an administrator as seen in FIG. 1. Moreover, the remote server is used to execute a number of internal software processes and store data for the present invention. The software processes may include, but are not limited to, server software programs, cloud software programs, web-based software applications or browsers embodied as, for example, but not be limited to, websites, web applications, cloud applications, desktop applications, and mobile applications compatible with a corresponding user PC device. Additionally, the software processes may store data into internal databases and communicate with external databases, which may include, but are not limited to, music databases (such as Apple iTunes®, Spotify®, Pandora®, etc.), music library databases, databases maintaining music genre information, databases maintaining user specific music files, etc. The interaction with external databases over a communication network may include, but is not limited to, the Internet.

As can be seen in FIG. 2, the music therapy informed method used to manage emotional regulation of the present invention manages at least one assessment of mood and music for a specific user with the corresponding PC device through the remote server, wherein the mood of the specific user is determined, and wherein the understanding of the association of music and mood is evaluated (Step B). The at least one assessment of mood and music delivers pre-generated inquiries to a user about the user's current mood, music, memory association, listening habits, and sensory preferences. With the specific mood information and adequate understanding of music associated with mood, the music therapy informed method recommends and relays a mood sequence formula (MSF) to the corresponding PC device of the specific user, wherein the MSF comprises at least one music medicine pill (MMP) which is a personalized sequence of music playlist from at least one music genre to manage the emotional regulation of the specific user, and wherein the plurality of music genres includes unsettled, smoothed, energized, theme and transition music (Step C). Subsequently, the music therapy informed method creates at least one MMP playlist based on the recommended MSF through the remote server, wherein the at least one MMP playlist comprises at a plurality of music pieces from the plurality of music genres (Step D), and sends and displays the at least one MMP playlist on the corresponding PC device of the specific user through the remote server.

Figure 3:
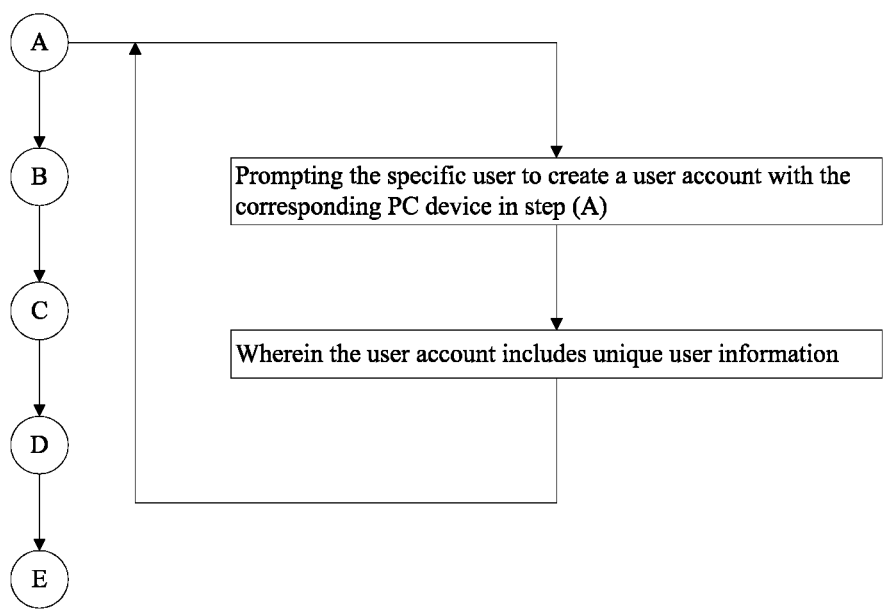
FIG. 3 is a flowchart diagram of a sub-process of creating a user account of the method of the present invention.
Figure 4:
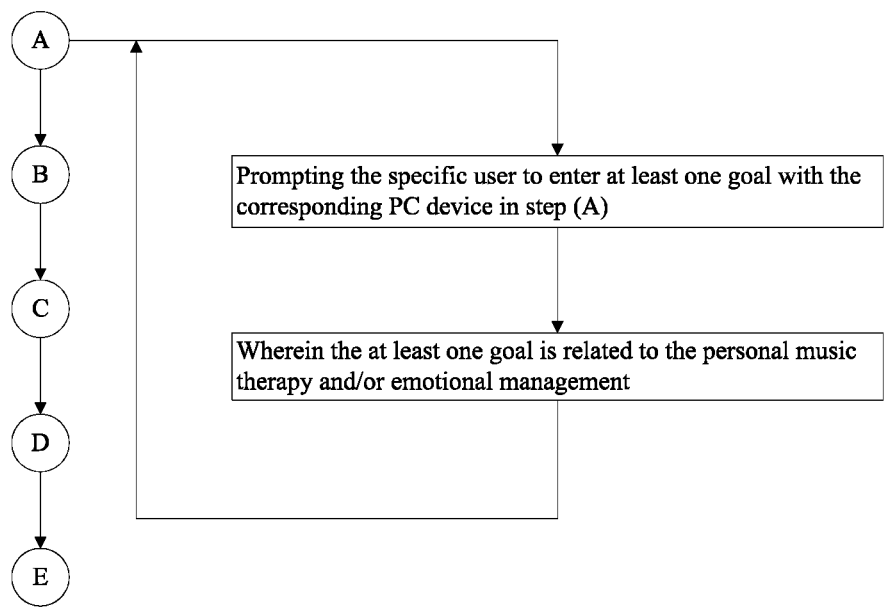
FIG. 4 is a flowchart diagram of a sub-process for a user to enter a goal in the method of the present invention.

As can be seen in FIG. 3, in an embodiment of the present invention, the music therapy informed method provides a sub-process for the specific user to create a user account. The embodiment of the music therapy informed method prompts the specific user to create a user account with the corresponding PC device in Step A, wherein the user account includes unique user information including, but not limited to, username, email address, zip code, region, etc. As can be seen in FIG. 4, in another embodiment the present invention, the music therapy informed method provides a sub-process for the specific user to enter at least one goal. More specifically, the music therapy informed method prompts the specific user to enter at least one goal with the corresponding PC device in step (A), wherein the at least one goal is related to the personal music therapy and/or emotional management, for example, improving sleep, getting motivated to lose weight, etc.

Figure 5:
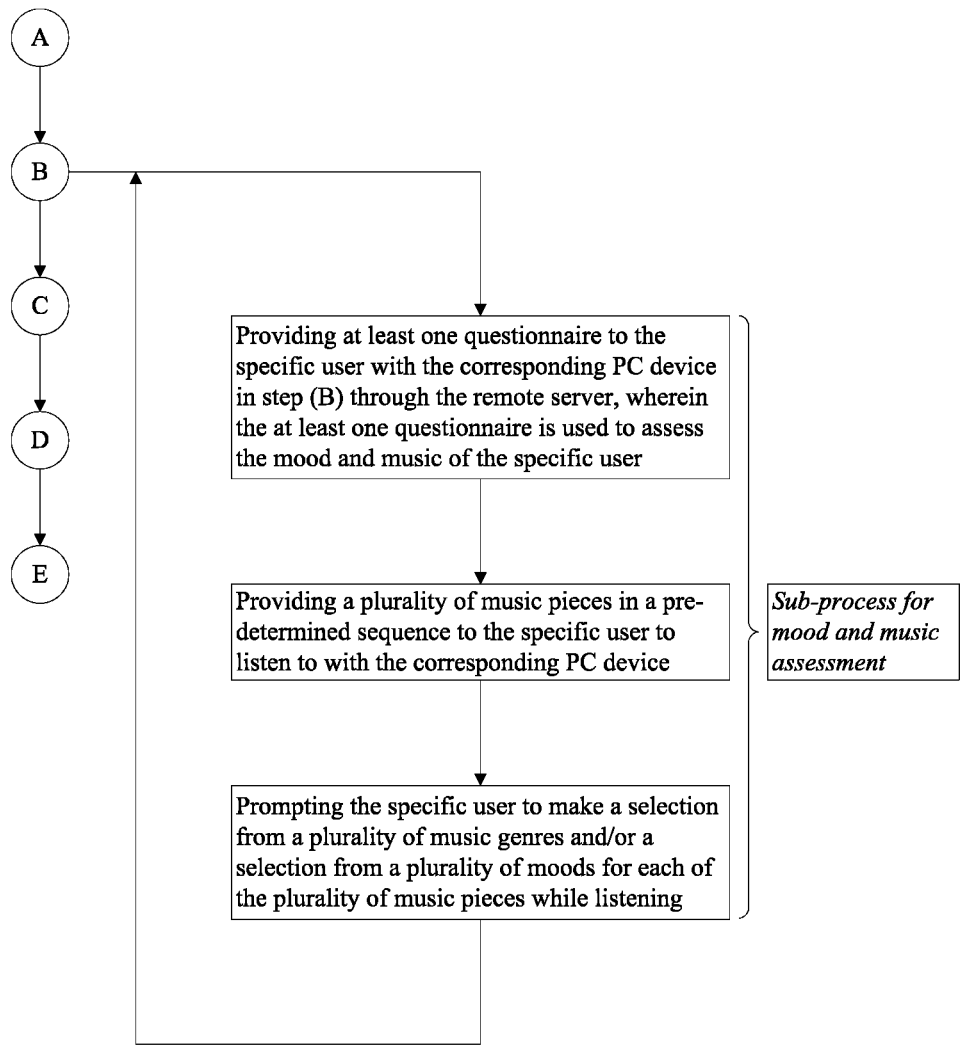
FIG. 5 is a flowchart diagram of a sub-process of mood and music assessment of the method of the present invention.

As can be seen in FIG. 5, in an embodiment of the present invention, the music therapy informed method provides a sub-process of mood and music assessment for the specific user. The mood and music assessment sub-process provides system guided assessments, a user self-assessment, and/or a combination thereof. More specifically, the music therapy informed method provides at least one questionnaire to the specific user with the corresponding PC device in Step B through the remote server, wherein the at least one questionnaire is used to assess the mood and music of the specific user. Then, the music therapy informed method provides a plurality of music pieces in a pre-determined sequence to the specific user to listen to with the corresponding PC device. Subsequently, the music therapy informed method prompts the specific user to make a selection from at least one music genre and/or a selection from a plurality of moods for each of the plurality of music pieces while listening. Thus, the mood and music assessment sub-process of the music therapy informed method can acquire substantial personal information of the specific user including past and/or current mood, music preference, understanding of the relationship between mood and music, etc.

Figure 6:
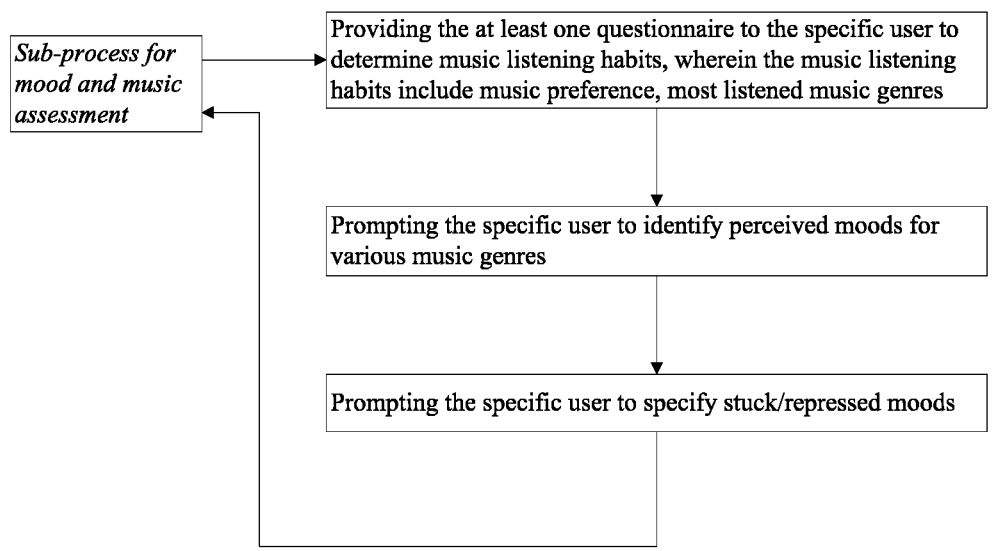
FIG. 6 is a flowchart diagram of an embodiment of the sub-process of mood and music assessment of the method of the present invention.

As can be seen in FIG. 6, in another embodiment of the present invention, the mood and music assessment sub-process of the music therapy informed method assesses the mood of the specific user. More specifically, the music therapy informed method provides the at least one questionnaire to the specific user to determine music listening habits, wherein the music listening habits include music preference, most listened music genres. Subsequently, the music therapy informed method prompts the specific user to identify perceived moods for various music genres, etc., and further, prompts the specific user to specify stuck/repressed moods, through inquiring about relevant values associative with the struck/repressed mood. Relevant values include timing, life events, music selection lyrics, music selection influence, mood state, and/or chronically unsettled comfort zones such as: anxiety versus excitement, anger versus energized, and depression versus calm.

Figure 7:
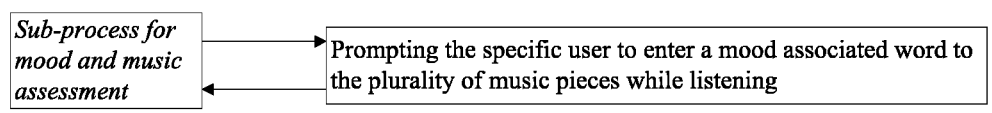
FIG. 7 is a flowchart diagram of another embodiment of the sub-process of mood and music assessment of the method of the present invention.
Figure 8:
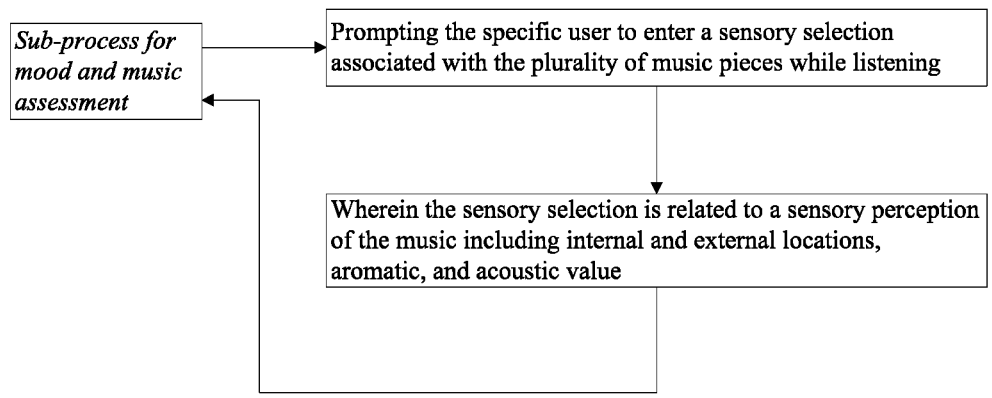
FIG. 8 is a flowchart diagram of another embodiment of the sub-process of mood and music assessment of the method of the present invention.

The user's understanding of the correlation between mood and music plays a critical role in this assessment and the subsequent formulation of MMP playlists. As can be seen in FIG. 7, in another embodiment of the present invention, the mood and music assessment sub-process of the music therapy informed method prompts the specific user to enter a mood associated word to the plurality of music pieces while listening. As can be seen in FIG. 8, in another embodiment of the present invention, the mood and music assessment sub-process of the music therapy informed method uses questionnaire to enable the specific user to enter sensory perceptions associated with the music therapy. More specifically, the music therapy informed method prompts the specific user to enter a sensory selection associated with the plurality of music pieces while listening, wherein the sensory selection is related to a sensory perception of the music including internal and external locations, aromatic, and acoustic values which are music elements including, but not limited to, pitch, melody, harmony, rhythm, tempo, vibrato, duration, texture, timbre, intensity.

Figure 9:
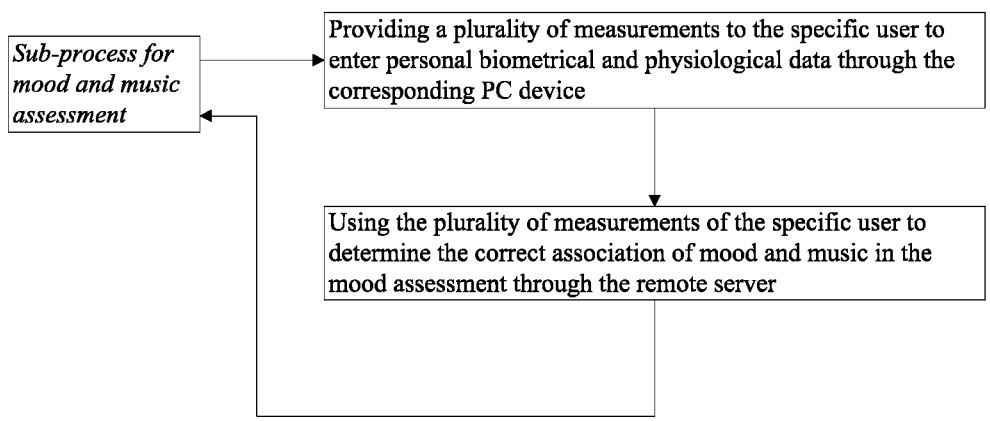
FIG. 9 is a flowchart diagram of another embodiment of the sub-process of mood and music assessment of the method of the present invention.

As can be seen in FIG. 9, in another embodiment of the present invention, the mood and music assessment sub-process of the music therapy informed method enables the specific user to enter biometrics and physiological measurements associated with the music therapy. More specifically, the music therapy informed method provides a plurality of measurements to the specific user to enter personal biometrical and physiological data through the corresponding PC device, and uses the plurality of measurements of the specific user to determine the correct association of mood and music in the mood assessment through the remote server. The plurality of measurements of the present invention includes, but is not limited to, galvanic skin responses, blood cortisol levels, blood pressure, pulse rate, eye dilation, physical activity, and any other relevant and viable physiological measures, etc. The mood and music assessment sub-process of the music therapy informed method includes self-assessment inquiries which produce user input data for targeting user preferences, strengthened by interface with app-based physiological tests such as real time cortisol measurement, blood pressure readings, galvanic skin response, and app-based emotional intelligence and performance tests to gauge/rank the biological, behavioral, and psychological impact of different music, empowering the user to maximize their benefits.

Figure 10:
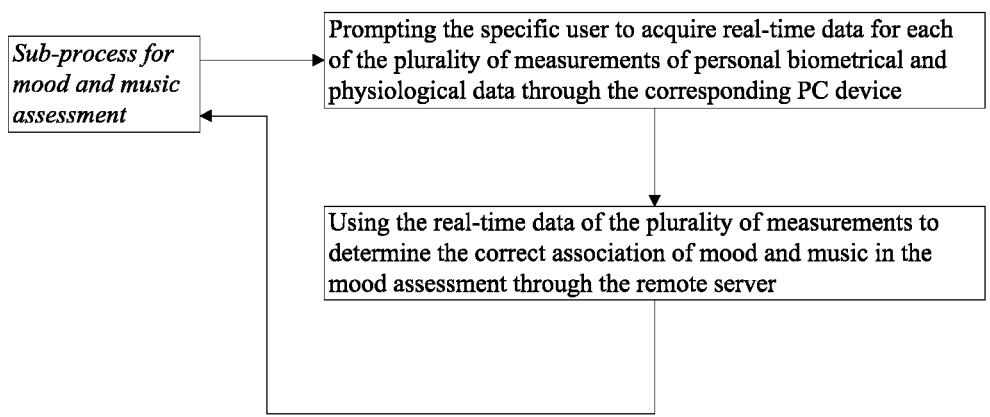
FIG. 10 is a flowchart diagram of another embodiment of the sub-process of mood and music assessment of the method of the present invention.

As can be seen in FIG. 10, in another embodiment of the present invention, the mood and music assessment sub-process of the music therapy informed method enables the specific user to directly acquire real-time biometrics and physiological measurements associated with the music therapy through measurement devices and instruments. More specifically, the music therapy informed method prompts the specific user to acquire real-time data for each of the plurality of measurements of personal biometrical and physiological data through the corresponding PC device, and uses the real-time data of the plurality of measurements to determine the correct association of mood and music in the mood assessment through the remote server. Examples of the measurement devices and instruments include heartbeat sensor, blood pressure meter, galvanic skin response device, blood cortisol level instrument, etc. Further, the music therapy informed method is able to integrate other apps and appliances which measure psychological, behavioral and physiological states such as: blood pressure, cortisol level, galvanic skin response to validate self-report data for user education, awareness and to maximize user benefits.

Figure 11:
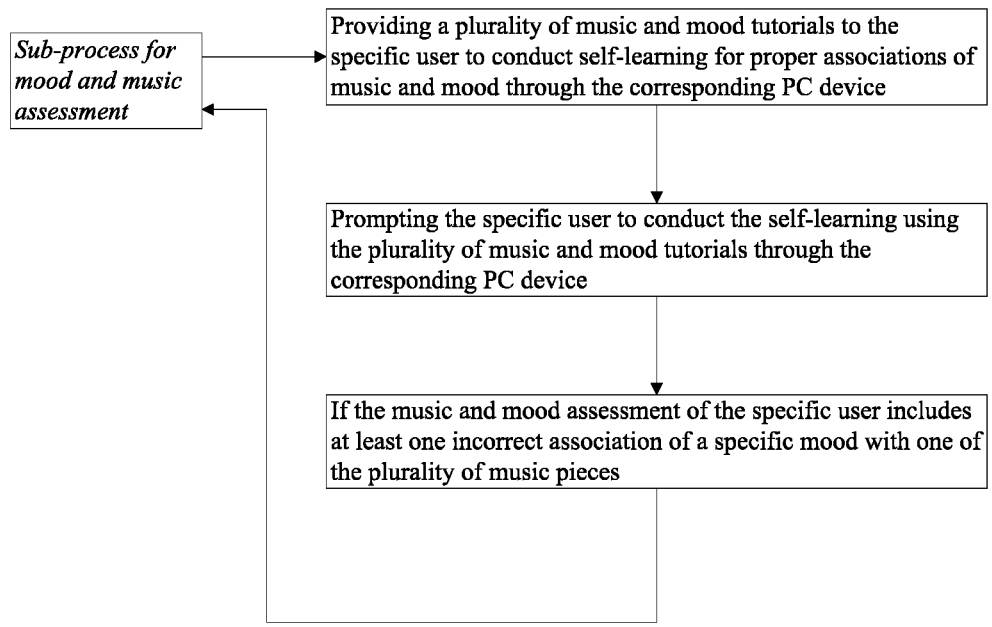
FIG. 11 is a flowchart diagram of another embodiment of the sub-process of mood and music assessment of the method of the present invention.

As can be seen in FIG. 11, in another embodiment of the present invention, the mood and music assessment sub-process of the music therapy informed method directs the specific user to a plurality of music and mood tutorials for self-learning to gain the fundamental understanding of the correlation of mood and music. More specifically, the music therapy informed method provides a plurality of music and mood tutorials to the specific user to conduct self-learning for proper associations of music and mood through the corresponding PC device. Then the music therapy informed method prompts the specific user to conduct the self-learning using the plurality of music and mood tutorials through the corresponding PC device, if the music and mood assessment of the specific user includes at least one incorrect association of a specific mood with one of the plurality of music pieces. Further, the plurality of music and mood tutorials can instruct the user about MSF, allowing them to understand the purpose of mood sequence formulas by guiding music listening through a cathartic mood change to reduce unsettledness and increase soothed and energized moods, shifting the user's mindset and mood to a positive state.

Figure 12:
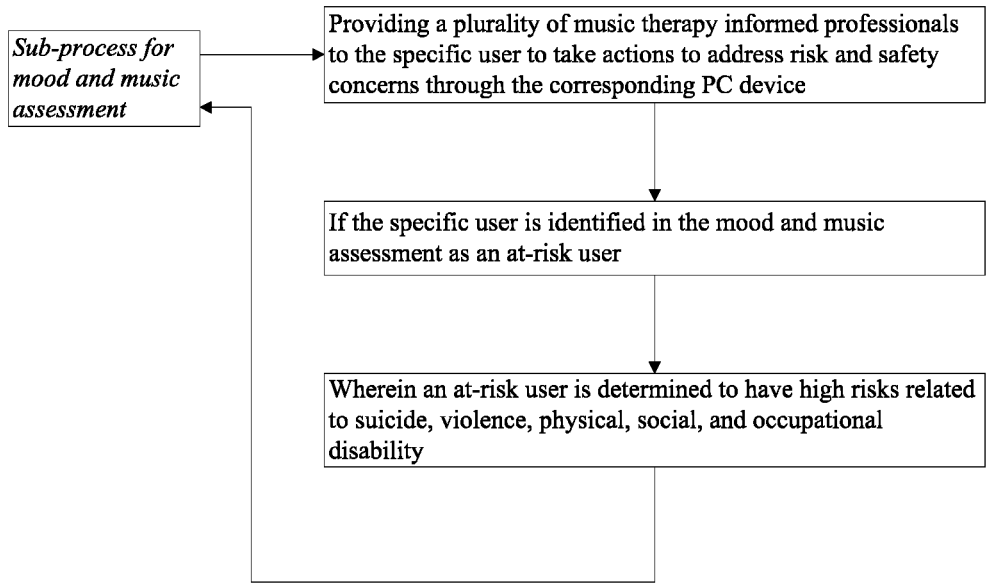
FIG. 12 is a flowchart diagram of another embodiment of the sub-process of mood and music assessment of the method of the present invention.

As can be seen in FIG. 12, in another embodiment of the present invention, the mood and music assessment sub-process of the music therapy informed method directs the specific user to a plurality of music therapy professionals for further assistance and/or consultation. More specifically, the music therapy informed method provides a plurality of music therapy professionals to the specific user to take actions to address risk and safety concerns through the corresponding PC device, if the specific user is identified in the mood and music assessment as an at-risk user, wherein an at-risk user is determined to have high risks related to suicide, violence, physical, social, and occupational disability.

Figure 13:
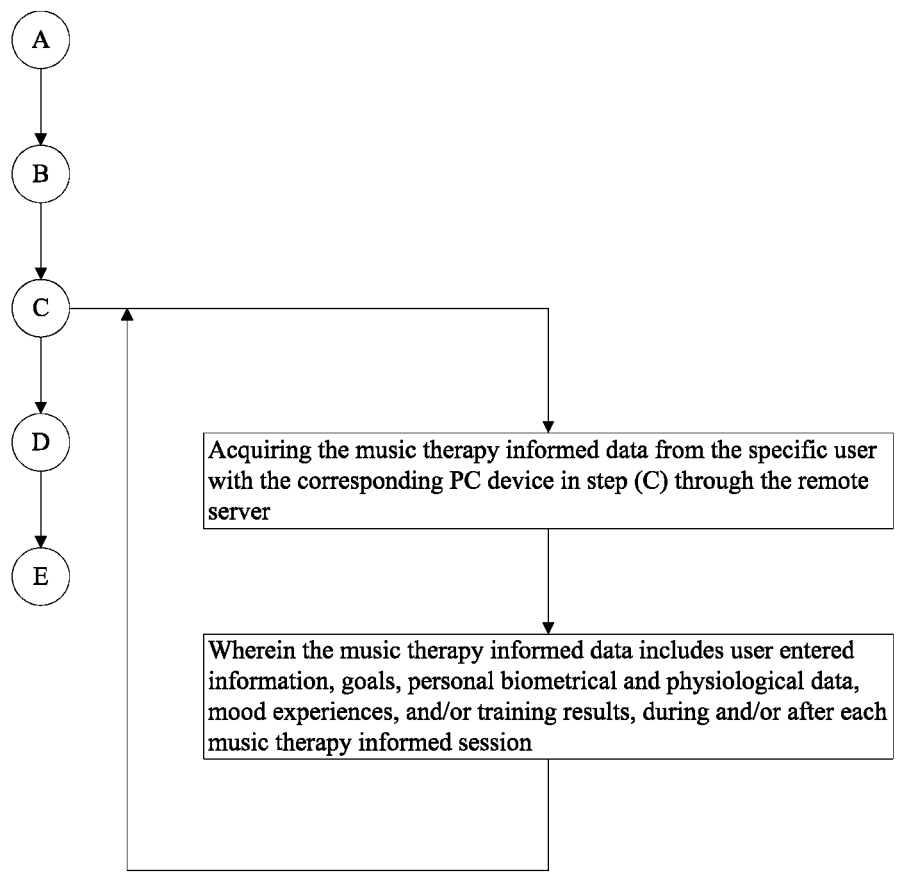
FIG. 13 is a flowchart diagram of a sub-process for acquiring and using actual therapy data in the method of the present invention.

As can be seen in FIG. 13, in another embodiment of the present invention, the music therapy informed method provides a sub-process to acquire and use therapy data for the specific user to be used to improve the MSF created by the present invention in Step C. More specifically, the music therapy informed method acquires music therapy informed data from the specific user with the corresponding PC device in Step C through the remote server, wherein the music therapy informed data includes user entered information, goals, personal biometrical and physiological data, mood experiences, and/or training results, during and/or after each music therapy informed session. The music therapy method provides efficient and effective means for the specific user to acquire music therapy informed information before, during, and after each session. This information includes ongoing training on the method, e-courses, and quizzes that reinforce the user's knowledge. In addition, the system captures music therapy informed data which may include, but is not limited to, a diary, personal notes, mood related words, quotes, goals, personal biometrical and physiological data, and/or training results, etc.

Figure 14:
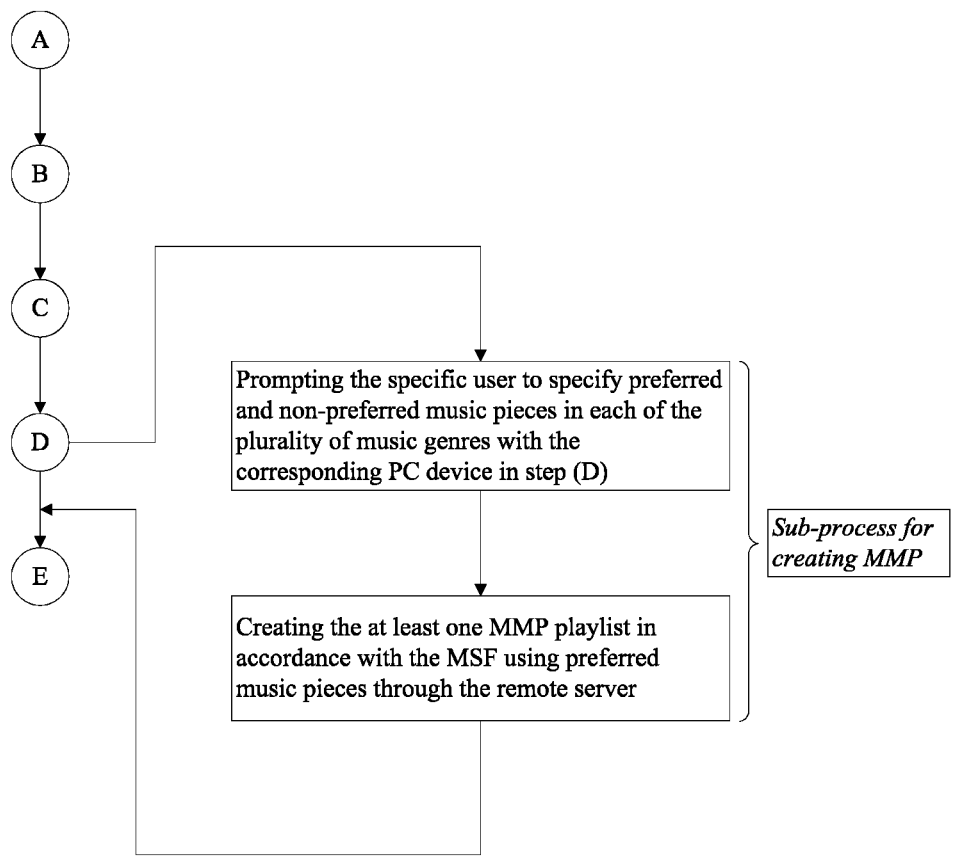
FIG. 14 is a flowchart diagram of a sub-process of creating a music medicine pill (MMP) in the method of the present invention.

As can be seen in FIG. 14, in another embodiment of the present invention, the music therapy informed method provides a sub-process for creating MMP playlists for the specific user in Step D. More specifically, the music therapy informed method prompts the specific user to specify preferred and non-preferred music pieces in each of the plurality of music genres with the corresponding PC device in Step D, and creates the at least one MMP playlist in accordance with the MSF using preferred music pieces through the remote server. The at least one MMP playlist can be created by the music therapy informed method of the present invention or by the specific user after proper training. Additionally, the present invention allows the specific user to specify personal mood music preference through the at least one assessment or entering preferences separately.

Figure 15:
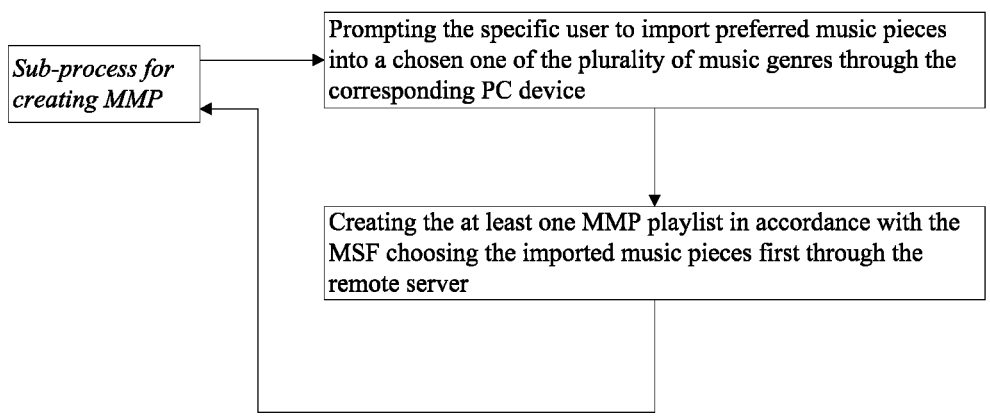
FIG. 15 is a flowchart diagram of an embodiment of the sub-process of creating a music medicine pill (MMP) in the method of the present invention.
Figure 16:
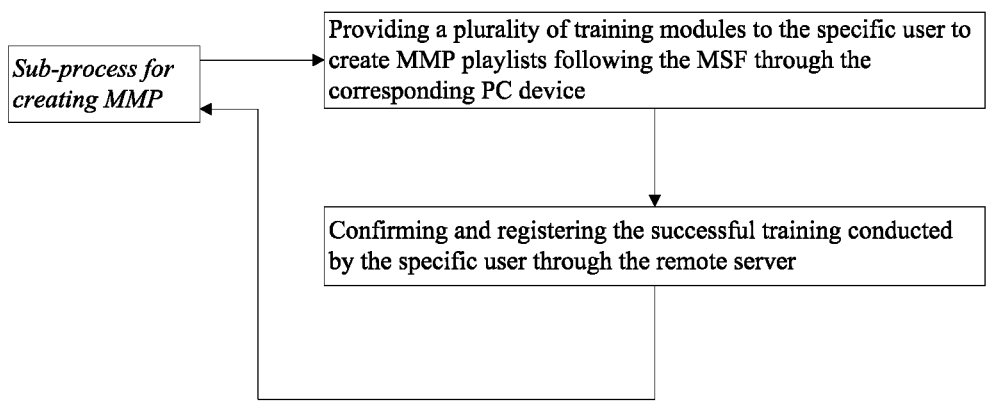
FIG. 16 is a flowchart diagram of another embodiment of the sub-process of creating a music medicine pill (MMP) in the method of the present invention.
Figure 17:
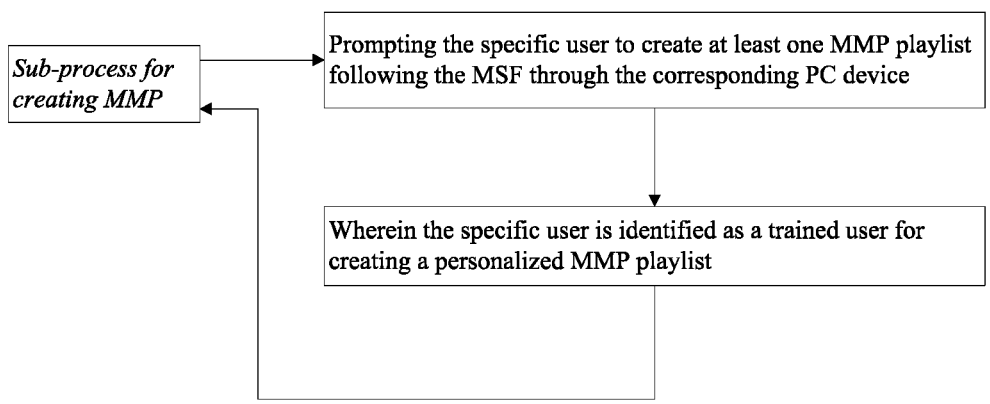
FIG. 17 is a flowchart diagram of another embodiment of the sub-process of creating a music medicine pill (MMP) in the method of the present invention.

As can be seen in FIG. 15, in another embodiment of the present invention, the creating MMP playlists sub-process of the music therapy informed method prompts the specific user to import preferred music pieces into a chosen one of the plurality of music genres through the corresponding PC device, and creates the at least one MMP playlist in accordance with the MSF choosing the imported music pieces first through the remote server. As can be seen in FIG. 16, in another embodiment of the present invention, the creating MMP playlists sub-process of the music therapy informed method provides a plurality of training modules to the specific user to create MMP playlists following the MSF through the corresponding PC device, and confirms and registers the successful training conducted by the specific user through the remote server. After the training, the specific user is confirmed and registered in the music therapy informed method of the present invention, the specific user is allowed to create at MMP playlists following the MSF created by the present invention. As can be seen in FIG. 17, in another embodiment of the present invention, the creating MMP playlists sub-process of the music therapy informed method prompts the specific user to create at least one MMP playlist following the MSF through the corresponding PC device, wherein the specific user is identified as a trained user for creating a personalized MMP playlist. The music therapy informed method allows the specific user to find and explore music selections associated with the external participating music platform application programs. Additionally, the music therapy informed method allows the specific user to search for their selected music selections. Further, the music therapy informed method provides at least one suggested imported music selection diet that comprises a minimum of one music selection for each specialized playlist, where each playlist equals the same approximate total music time for a balanced music diet. The music therapy informed method of the present invention supports a balanced music diet which addresses the broad emotional continuum of negative and positive moods generalized within the three specialized playlists entitled Unsettled, Soothed, and Energized mood categories. Specific emotions are found within each mood category. Moods last a long time, hours or days, with no identifiable object, and lack intensity. Emotions last a short time, relate to a person or situation, and are identified and felt intensely, such as the emotions including, but not limited to, being happy, hopeful, terror, despair or exhilaration, etc. When a bad mood is experienced, negative emotions are evoked of fear, anger or sadness about something. Conversely, when a good mood is experienced, positive emotions are elicited of feeling peaceful, optimistic or happy about something. The mood may not be consciously considered until the emotional reaction to a situation is considered. Then, emotions inform the mood. Targeted moods and emotions, both problematic (i.e. stuck, repressed or suppressed) and desired, are identified by the user during this music therapy informed method. Music is matched to those moods and emotions with the end result being a balanced diet which allows each mood category the essential equal time for elicitation and release of all identified moods and emotions. When the balanced diet is implemented strategically with MER, emotional fluidity is the desired outcome. Emotional fluidity allows the user to become more fluid in the way that moods and emotions are experienced and communicated, building the user's capacity to move easily from one mood or emotion to another. Being able to connect with targeted moods and emotions across the broad emotional continuum, and then release them, equips the user with emotional fluidity and greater capacity to deal with more stress.

Figure 18:
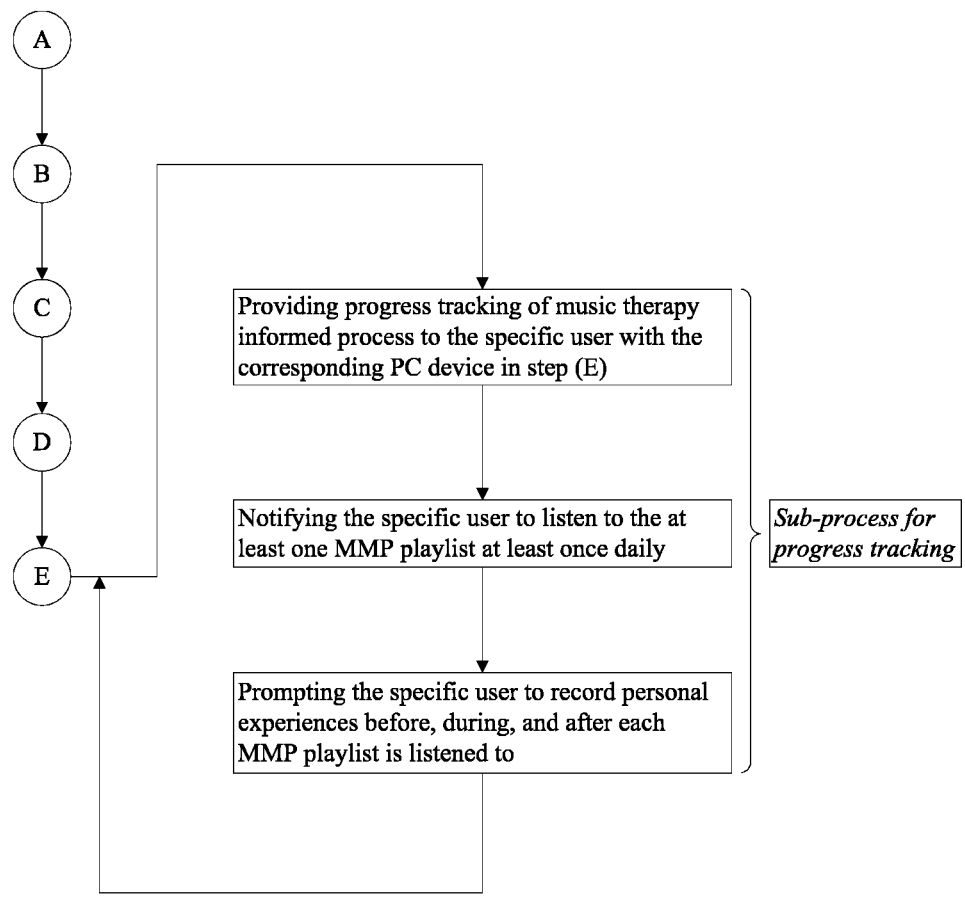
FIG. 18 is a flowchart diagram of a sub-process of progress tracking in the method of the present invention.
Figure 19:
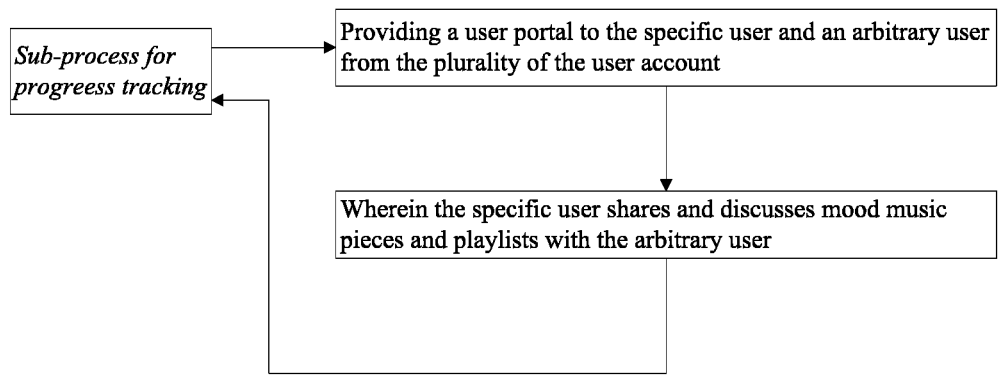
FIG. 19 is a flowchart diagram of an embodiment of the sub-process of progress tracking in the method of the present invention.
Figure 20:
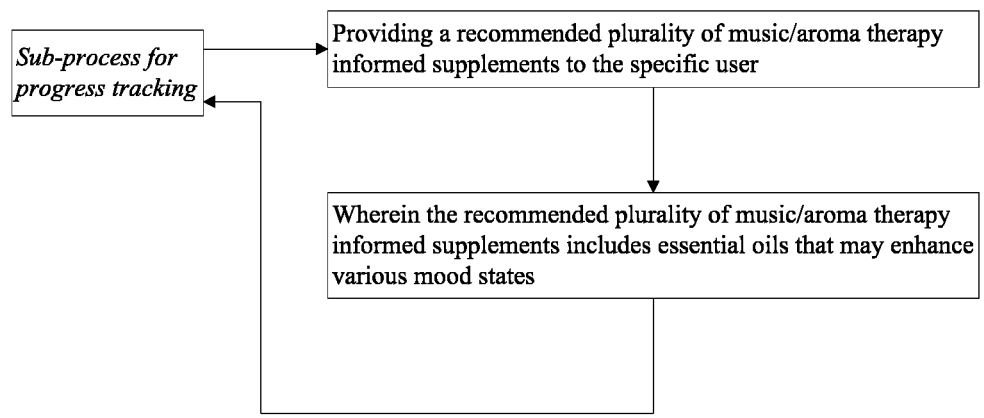
FIG. 20 is a flowchart diagram of another embodiment of the sub-process of progress tracking in the method of the present invention.

As can be seen in FIG. 18, in another embodiment of the present invention, the music therapy informed method provides a sub-process for tracking the progress for the specific user in Step E. More specifically, the music therapy informed method provides progress tracking of music therapy informed process to the specific user with the corresponding PC device in Step E by notifying the specific user to listen to the at least one MMP playlist at least once daily, and prompting the specific user to record personal experiences before, during, and after each MMP playlist is listened to. Additionally, the music therapy informed method enables the specific user to communicate with others and share personal music therapy experiences through a user portal of the present invention. As can be seen in FIG. 19, in another embodiment of the present invention, the progress tracking sub-process of the music therapy informed method provides a user portal to the specific user and an arbitrary user from the plurality of the user account, wherein the specific user shares and discusses mood music pieces and playlists with the arbitrary user. Further, the present invention can make recommendations regarding the use of supplements with the music therapy to enhance the effectiveness of the MMP playlists. The music therapy informed method also allows the specific user to view results associated with the assessment. Additionally, the specific user is enabled to view the progress of their goals derived from the education module. As can be seen in FIG. 20, in another embodiment of the present invention, the progress tracking sub-process of the music therapy informed method provides a recommended plurality of music/aroma therapy informed supplements to the specific user, wherein the recommended plurality of music/aroma therapy informed supplements includes essential oils that may enhance various mood states.

Figure 21:
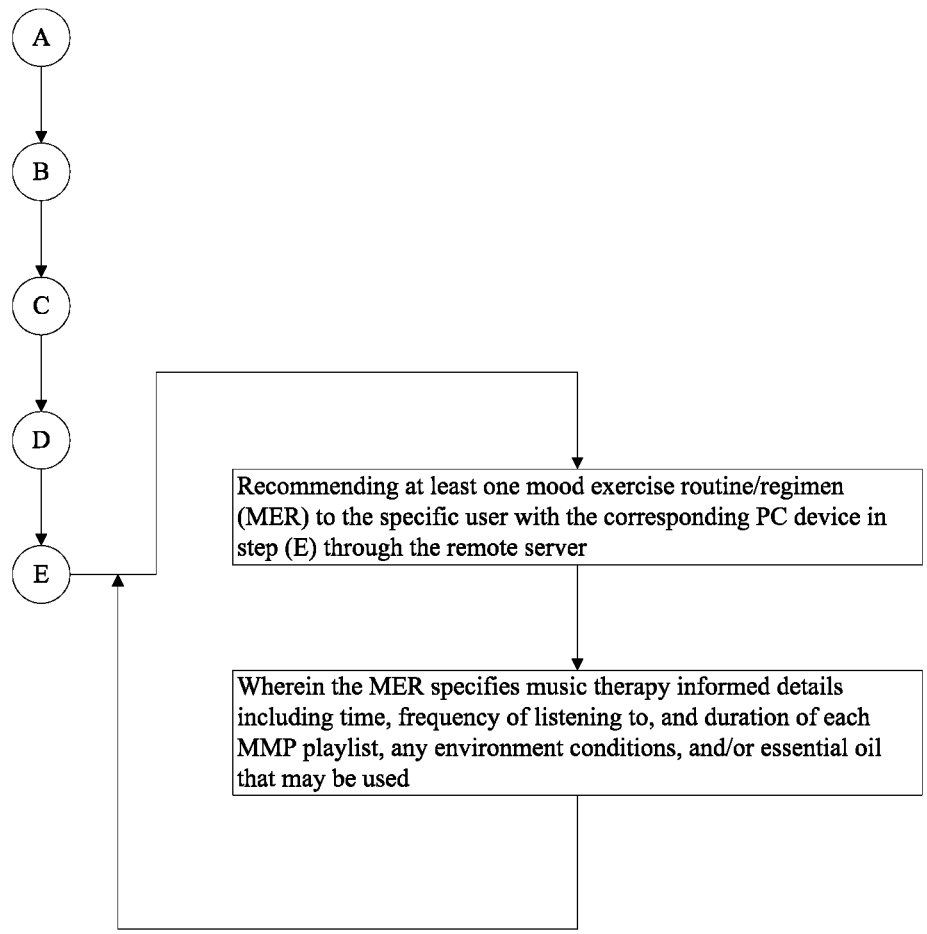
FIG. 21 is a flowchart diagram of a sub-process of recommending a mood exercise routine/regimen (MER) in the method of the present invention.

As can be seen in FIG. 21, in another embodiment of the present invention, the music therapy informed method provides a sub-process for recommending a mood exercise routine/regimen to the specific user in Step E. More specifically, the music therapy informed method recommends at least one mood exercise routine/regimen (MER) to the specific user with the corresponding PC device in Step E through the remote server, wherein the MER specifies music therapy informed details including time, frequency of listening to, and duration of each MMP playlist, any environment conditions, and/or essential oil that may be used. The MER includes necessary and detailed guidance and instruction that the present invention recommends to the specific user to make the best use of the MMP playlists and accomplish specific goals. Additionally, the music therapy informed method provides the specific user with daily, personalized pieces of music along with an inspirational quote to help drive them toward an improved mental state.

Although the invention has been explained in relation to its preferred embodiment, it is to be understood that many other possible modifications and variations can be made without departing from the spirit and scope of the invention as hereinafter claimed.

What is claimed is:
1. A method comprising:
providing to users a plurality of user accounts managed by a remote server, wherein each of the plurality of user accounts and each of the users are associated with a corresponding personal computing (PC) device;
managing a mood assessment and a music assessment for a user with the corresponding PC device through the remote server, wherein a mood of the user is determined, and wherein an understanding of an association of music with the mood is evaluated;

creating a mood sequence formula (MSF) comprising a playlist of target music associated with the mood of the user, wherein the MSF comprises an evaluation and identification of listening habits of the user, personal mood music experiences of the user, and the understanding of the association of music with the mood and personal goals of the user;

recommending and relaying the MSF to the corresponding PC device of the user, creating a music medicine pill (MMP) playlist that comprises the recommended MSF, wherein the MMP playlist is a personalized sequence of music from a music playlist from one or more music genres to manage an emotional regulation of the user, wherein the one or more music genres include at least one of unsettled, soothed, energized, theme or transition music;

prompting the user to import, through the corresponding PC device, preferred music pieces of a plurality of music pieces into a storage location for a chosen one of the one or more music genres;

creating the MMP playlist comprising the MSF and the preferred music pieces of the plurality of music pieces; and displaying the MMP playlist on the corresponding PC device of the user.

2. The method of claim 1, further comprising prompting each of the users to create each of the plurality of user accounts with the corresponding PC device, wherein each of the plurality of user accounts includes unique user information.

3. The method of claim 1, further comprising prompting the user to enter at least one goal of the personal goals of the user, with the corresponding PC device, wherein the at least one goal is related to at least one of personal music therapy or emotional management.

4. The method of claim 1, further comprising:
providing a questionnaire to the user with the corresponding PC device through the remote server, wherein the questionnaire is used to assess the mood and music for the user;
providing the plurality of music pieces in a pre-determined sequence to the user to listen to with the corresponding PC device; and
prompting the user to make at least one of a selection from the one or more music genres or a selection from a plurality of moods for each of the plurality of music pieces while listening.

5. The method of claim 1, further comprising:
providing the user a questionnaire to determine the listening habits, wherein the listening habits include at least one of music preference or most listened of the one or more music genres;
prompting the user to identify perceived moods for the one or more music genres; and
prompting the user to specify stuck/repressed moods.

6. The method of claim 1, further comprising prompting the user to enter a mood associated word to the plurality of music pieces while listening.

7. The method of claim 1, further comprising prompting the user to enter a sensory selection associated with the plurality of music pieces while listening, wherein the sensory selection is related to a sensory perception of the music that includes external locations, internal locations, aromatic values and acoustic values.

8. The method of claim 1, further comprising:
providing a plurality of measurements to the user to enter personal biometrical and physiological data through the corresponding PC device; and
determining a correct association of the mood and music in the mood assessment using the plurality of measurements of the user.

9. The method of claim 1, further comprising:
prompting the user to acquire real-time data for each of a plurality of measurements of personal biometrical and physiological data through the corresponding PC device; and
determining a correct association of the mood and music in the mood assessment using the real-time data of the plurality of measurements.

10. The method of claim 1, further comprising:
providing a plurality of music and mood tutorials to the user to conduct self-learning for the association of music and the mood through the corresponding PC device; and
prompting the user to conduct the self-learning by using the plurality of music and mood tutorials through the corresponding PC device, in response to the mood assessment and the music assessment of the user including an incorrect association of the mood of the user with one of the plurality of music pieces.

11. The method of claim 1, further comprising providing a plurality of music therapy informed professionals to the user to take actions to address risk and safety concerns through the corresponding PC device, in response to the user being identified in the mood assessment and the music assessment as an at-risk user, wherein the at-risk user is determined to have high risks related to suicide, violence, physical, social, and occupational disability.

12. The method of claim 1, further comprising acquiring music therapy informed data from the user with the corresponding PC device through the remote server, wherein the music therapy informed data includes at least one of user entered information, at least one goal of the personal goals of the user, personal biometrical data, physiological data, mood experiences, or training results.

13. The method of claim 1, further comprising prompting the user to specify the preferred music pieces and non-preferred music pieces of the plurality of music pieces in each of the one or more music genres with the corresponding PC device.

14. The method of claim 1, further comprising:
prompting a plurality of training modules to the user to create the MMP playlist comprising the recommended MSF; and
confirming and registering successful training conducted by the user through the remote server.

15. The method of claim 1, further comprising prompting the user to create the MMP playlist comprising the recommended MSF through the corresponding PC device, wherein the user is identified as a trained user for creating the MMP playlist.

16. The method of claim 1, further comprising providing a user portal to the user and an arbitrary user from the plurality of user accounts, wherein the user shares and discusses the plurality of music pieces and the MMP playlist with the arbitrary user.

17. The method of claim 1, further comprising providing a recommended plurality of supplements to the user, wherein the recommended plurality of supplements comprise enhancements to music/aroma therapy, and wherein the recommended plurality of supplements includes essential oils that enhance various mood states.

18. The method of claim 1, further comprising recommending a mood exercise routine/regimen (MER) to the user with the corresponding PC device, wherein the MER specifies music therapy details including at least one of time, frequency of listening to, and duration of the MMP playlist, any environment conditions, or essential oils.

19. A method comprising:
- providing to users a plurality of user accounts managed by a remote server, wherein each of the plurality of user accounts and each of the users are associated with a corresponding personal computing (PC) device;
- managing a mood assessment and a music assessment for a user with the corresponding PC device through the remote server, wherein a mood of the user is determined, and wherein an understanding of an association of music with the mood is evaluated;
- creating a mood sequence formula (MSF) comprising a playlist of target music associated with the mood of the user,
- wherein the MSF comprises an evaluation and identification of listening habits of the user, personal mood music experiences of the user, and the understanding of the association of music with the mood and personal goals of the user,
- creating a music medicine pill (MMP) playlist comprising the MSF, wherein the MMP playlist comprises a plurality of music pieces from the one or more music genres,
- wherein the MSF comprises the MMP playlist which is a personalized sequence of music from a music playlist from one or more music genres to manage an emotional regulation of the user, wherein the one or more music genres includes at least one of unsettled, soothed, energized, theme or transition music;
- displaying the MMP playlist on the corresponding PC device of the user;
- notifying the user to listen to the MMP playlist at least once daily;
- providing progress tracking of the listening to the MMP playlist at least once daily; and
- prompting the user to record personal experiences before, during, and after the MMP playlist is listened to.

* * * * *